(12) United States Patent
Minami et al.

(10) Patent No.: US 11,261,089 B2
(45) Date of Patent: Mar. 1, 2022

(54) ANHYDROUS DIBASIC CALCIUM PHOSPHATE, AND METHOD FOR PRODUCING SAME

(71) Applicant: Tomita Pharmaceutical Co., Ltd., Naruto (JP)

(72) Inventors: Shota Minami, Naruto (JP); Akihito Bando, Naruto (JP)

(73) Assignee: Tomita Pharmaceutical Co., Ltd.

( * ) Notice: Subject to any disclaimer, the term of this patent is extended or adjusted under 35 U.S.C. 154(b) by 260 days.

(21) Appl. No.: 16/499,045

(22) PCT Filed: Mar. 23, 2018

(86) PCT No.: PCT/JP2018/011740
§ 371 (c)(1),
(2) Date: Sep. 27, 2019

(87) PCT Pub. No.: WO2018/181006
PCT Pub. Date: Oct. 4, 2018

(65) Prior Publication Data
US 2020/0031669 A1    Jan. 30, 2020

(30) Foreign Application Priority Data
Mar. 30, 2017 (JP) .............................. JP2017-068089

(51) Int. Cl.
*C01B 25/32* (2006.01)
*A61K 8/24* (2006.01)
*A23L 33/16* (2016.01)

(52) U.S. Cl.
CPC ................ *C01B 25/32* (2013.01); *A61K 8/24* (2013.01); *A23L 33/16* (2016.08); *A23V 2002/00* (2013.01)

(58) Field of Classification Search
CPC ...................................................... C01B 25/32
USPC ......................................................... 423/305
See application file for complete search history.

(56) References Cited

U.S. PATENT DOCUMENTS

| 4,203,955 A | 5/1980 | Enomoto et al. |
| 4,707,361 A | 11/1987 | Gustafson et al. |
| 5,486,365 A | 1/1996 | Takado et al. |
| 2006/0013921 A1 | 1/2006 | Kasahara et al. |

FOREIGN PATENT DOCUMENTS

| CN | 106006594 A | 10/2016 |
| CN | 108046228 A | 5/2018 |
| EP | 2 208 705 A1 | 7/2010 |
| JP | S51-031238 A | 9/1976 |

(Continued)

OTHER PUBLICATIONS

International Search Report in International Application No. PCT/JP2018/011740, dated Apr. 17, 2018.

(Continued)

*Primary Examiner* — Melissa S Swain
(74) *Attorney, Agent, or Firm* — Knobbe, Martens, Olson & Bear, LLP (57) ABSTRACT

An object of the present invention is to provide anhydrous dibasic calcium phosphate having good powder flowability and good dispersibility in water. An anhydrous dibasic calcium phosphate powder containing agglomerated particles formed by agglomerating anhydrous dibasic calcium phosphate particles having a modal pore diameter/mean particle diameter ratio of 0.2 to 0.34 exhibits good powder flowability and good dispersibility in water.

10 Claims, 4 Drawing Sheets

Example 3

(56) References Cited

FOREIGN PATENT DOCUMENTS

| | | |
|---|---|---|
| JP | S59-207818 A | 11/1984 |
| JP | S59-223204 A | 12/1984 |
| JP | S59-223206 A | 12/1984 |
| JP | S59-223208 A | 12/1984 |
| JP | S62-036010 A | 2/1987 |
| JP | H06-298505 A | 10/1994 |
| JP | H07-033670 A | 2/1995 |
| JP | H07-118005 A | 5/1995 |
| JP | 2009-029693 A | 2/2009 |
| JP | 2016-069243 A | 5/2016 |

OTHER PUBLICATIONS

Supplementary European Search Report, EP Patent Application No. 18774712.6, dated Nov. 19, 2020.
Taiwanese Office Action issued in Taiwan Patent Application No. 107110039, dated Oct. 27, 2021.

Fig. 1
Example 3

Fig. 2
Example 7

Fig. 3

Comparative Example 1

Fig. 4

Example 9

Fig. 5

Example 11

Fig. 6

Comparative Example 5

Fig. 7

Comparative Example 6

Fig. 8

Example 9, Comparative Example 5, Comparative Example 6

ANHYDROUS DIBASIC CALCIUM PHOSPHATE, AND METHOD FOR PRODUCING SAME

TECHNICAL FIELD

The present invention relates to anhydrous dibasic calcium phosphate having good powder flowability and good dispersibility in a liquid, and a method for producing the anhydrous dibasic calcium phosphate.

BACKGROUND ART

In recent years, food or beverage products fortified with nutrients, such as vitamins or minerals, have been sold owing to the increasing health consciousness. Minerals, in particular, which are essential to maintain life, cannot be produced within a human body and hence, need to be taken from daily meals. Calcium, among various minerals, is an important ion that is not only essential for the growth of bone, but is also involved in physiological functions, such as transmission of nerve stimuli, muscle contraction, blood coagulation, and regulation of many enzymes or enzyme systems. However, even in today's dietary lifestyle called the age of satiation, calcium is one of nutrients that tend to be deficient, and at present, calcium is fortified even in milk and dairy products, such as fermented milk or lactic acid bacteria beverages, which are relatively rich in calcium. Calcium carbonate, calcium phosphate, calcium citrate, calcium gluconate, and the like are known as additives used for calcium fortification. Especially anhydrous dibasic calcium phosphate, which is not hygroscopic, shows a neutral pH as an aqueous suspension, and is inert, has long been used as excipients or additives for pharmaceutical products, cosmetic products, food products, and the like.

While it is known that dibasic calcium phosphate is produced as plate-like particles having a low bulk specific volume, attempts have been recently made to improve the powder physical properties by increasing the bulk specific volume, by adding a crystal habit modifier, such as a polyvalent organic acid.

Patent Literature 1, for example, proposes a method in which sodium hydroxide is added when hydrous dibasic calcium phosphate is suspended in water and thermally decomposed, in order to obtain anhydrous dibasic calcium phosphate suitable as an excipient for direct tableting of pharmaceutical products. The anhydrous dibasic calcium phosphate produced by adding an alkali, as disclosed in Patent Literature 1, is microcrystalline particles, and is in the form of a fine powder, and therefore, can exhibit a high binding force when it is subjected to compression molding; on the other hand, it has the disadvantage of having a high powder bulk specific volume, and having low powder flowability and hence, poor handleability.

Patent Literature 2 proposes a method in which phosphoric acid, an alkaline calcium compound or alkali metal salt, and a calcium compound are reacted in an aqueous medium in the presence of a polyvalent organic acid having a coordination ability to produce columnar dibasic calcium phosphate, and the columnar dibasic calcium phosphate is subsequently hydrothermally treated at 60° C. or more, for the purpose of obtaining dibasic calcium phosphate having good binding properties, which can be suitably used as an excipient for pharmaceutical products and the like. The dibasic calcium phosphate obtained by the technique of Patent Literature 2 is useful as an excipient that is composed of small crystalline particles, and is high in all of bulk specific volume, surface area, and oil absorption quantity; however, the use of the polyvalent organic acid in the production process may possibly cause limitations on the equipment or the inclusion of impurities in the final product. The dibasic calcium phosphate obtained by the technique of Patent Literature 2, which is particles, and has a high bulk specific volume, has the disadvantage of having poor powder flowability. Such a powder having low flowability has high adhesion properties and high cohesion, and therefore, may possibly invite phenomena such as clogging of the powder on a transfer line; a bridge in which particles of the powder form an arch structure to clog at the outlet of a hopper, and the powder cannot be discharged through the outlet; and a rat-hole in which the powder forms a hard solid around the discharge layer of the powder, and the powder stops the discharge. This may cause adverse effects, such as a reduction in production efficiency, in the production of the powder per se or in the production of food products or pharmaceutical products using the powder.

CITATION LIST

Patent Literature

Patent Literature 1: JP S51-31238 B
Patent Literature 2: JP H7-118005 A

SUMMARY OF INVENTION

Technical Problem

It is important for dibasic calcium phosphate, which is applied to the production of pharmaceutical products, cosmetic products, food products, and the like, to have high powder flowability and good handleability. Dibasic calcium phosphate is also required to have good dispersibility in a liquid, because it may be dispersed in the liquid, in the form of a final product or a production intermediate.

Accordingly, it is an object of the present invention to provide anhydrous dibasic calcium phosphate having good powder flowability and good dispersibility in a liquid. It is another object of the present invention to provide a method for producing the anhydrous dibasic calcium phosphate.

Solution to Problem

As a result of extensive research to solve the above-mentioned problem, the inventors of the present invention has obtained the following findings: First, the inventors have found that anhydrous dibasic calcium phosphate particles obtained through the following first to third steps have a modal pore diameter/mean particle diameter ratio of 0.2 to 0.34, as determined by a mercury porosimeter, and have physical properties different from those of previously reported anhydrous dibasic calcium phosphate particles:

(a) a first step of preparing a calcium hydroxide-containing solution, wherein the calcium hydroxide-containing solution contains calcium hydroxide and calcium ions, and a molar ratio of calcium atoms present as the calcium ions, relative to calcium atoms constituting the calcium hydroxide, is 0.04 to 0.16;

(b) a second step of adding phosphoric acid to the calcium hydroxide-containing solution obtained in the first step to obtain a first dibasic calcium phosphate-containing solution; and (c) a third step of adding an alkali metal hydroxide to the first dibasic calcium phosphate-containing solution obtained in the second step, wherein the amount of the alkali metal hydroxide to be added is adjusted to 1.5 to 13.0 mol per mole of the calcium atoms present as the calcium ions in the calcium hydroxide-containing solution prepared in the first step, to obtain a second dibasic calcium phosphate-containing solution.

Subsequently, the inventors have found that an anhydrous dibasic calcium phosphate powder containing agglomerated particles formed by agglomerating the anhydrous dibasic calcium phosphate particles has good powder flowability and good dispersibility in a liquid. The present invention has been completed by conducting further research based on these findings.

In summary, the present invention provides aspects of invention as itemized below.

Item 1. A method for producing anhydrous dibasic calcium phosphate comprising the following steps:
(a) a first step of preparing a calcium hydroxide-containing solution, wherein the calcium hydroxide-containing solution contains calcium hydroxide and calcium ions, and a molar ratio of calcium atoms present as the calcium ions, relative to calcium atoms constituting the calcium hydroxide, is 0.04 to 0.16;
(b) a second step of adding phosphoric acid to the calcium hydroxide-containing solution obtained in the first step to obtain a first dibasic calcium phosphate-containing solution; and
(c) a third step of adding an alkali metal hydroxide to the first dibasic calcium phosphate-containing solution obtained in the second step, wherein the amount of the alkali metal hydroxide to be added is adjusted to 1.5 to 13.0 mol per mole of the calcium atoms present as the calcium ions in the calcium hydroxide-containing solution prepared in the first step, to obtain a second dibasic calcium phosphate-containing solution.

Item 2. The method for producing anhydrous dibasic calcium phosphate according to item 1, wherein the first step is the step of obtaining the calcium hydroxide-containing solution, by allowing a soluble calcium salt and an alkali metal hydroxide to coexist in water such that a molar ratio of alkali metal atoms relative to calcium atoms becomes 1.73 to 1.91, and
the third step is the step of adding the alkali metal hydroxide to the first dibasic calcium phosphate-containing solution obtained in the second step, until a molar ratio of alkali metal atoms relative to calcium atoms in the solution becomes 1.95 to 2.5, to obtain the second dibasic calcium phosphate-containing solution.

Item 3. The method for producing anhydrous dibasic calcium phosphate according to item 1 or 2, wherein the alkali metal hydroxide is sodium hydroxide.

Item 4. The method for producing anhydrous dibasic calcium phosphate according to any one of items 1 to 3, wherein solids are collected from the second dibasic calcium phosphate-containing solution obtained in the third step, and subjected to a drying treatment.

Item 5. Anhydrous dibasic calcium phosphate particles having a ratio of modal pore diameter to mean particle diameter of 0.2 to 0.34, as determined by a mercury porosimeter.

Item 6. The anhydrous dibasic calcium phosphate particles according to item 5, wherein the anhydrous dibasic calcium phosphate particles have a mean particle diameter of 1 μm or more and less than 10 μm.

Item 7. The anhydrous dibasic calcium phosphate particles according to item 5 or 6, wherein the anhydrous dibasic calcium phosphate particles have a static bulk specific volume of 40 mL/10 g or less.

Item 8. The anhydrous dibasic calcium phosphate particles according to any one of items 5 to 7, wherein the anhydrous dibasic calcium phosphate particles have an anhydrous dibasic calcium phosphate content of 97% or more.

Item 9. An anhydrous dibasic calcium phosphate powder comprising agglomerated particles in which the anhydrous dibasic calcium phosphate particles according to any one of items 5 to 8 are agglomerated.

Item 10. The anhydrous dibasic calcium phosphate powder according to item 9, wherein the anhydrous dibasic calcium phosphate powder has an angle of repose of 45° or less.

Advantageous Effects of Invention

The anhydrous dibasic calcium phosphate powder according to the present invention has excellent flowability, and has good handleability when it is used as various additives or ingredients for food products, cosmetic preparations, pharmaceuticals, and the like. Moreover, the anhydrous dibasic calcium phosphate powder according to the present invention, despite being composed of agglomerated particles, has good dispersibility in a liquid, because the agglomerated particles have weak cohesion, such that the agglomerated state is easily loosened by a stirring treatment, an ultrasonic treatment, or the like in water, and turns into a minutely dispersed state.

Furthermore, the anhydrous dibasic calcium phosphate particles and the anhydrous dibasic calcium phosphate powder according to the present invention have a high dibasic calcium phosphate content, and thus, can also be utilized as anhydrous dibasic calcium phosphate with high purity.

DESCRIPTION OF EMBODIMENTS

Figure 2:
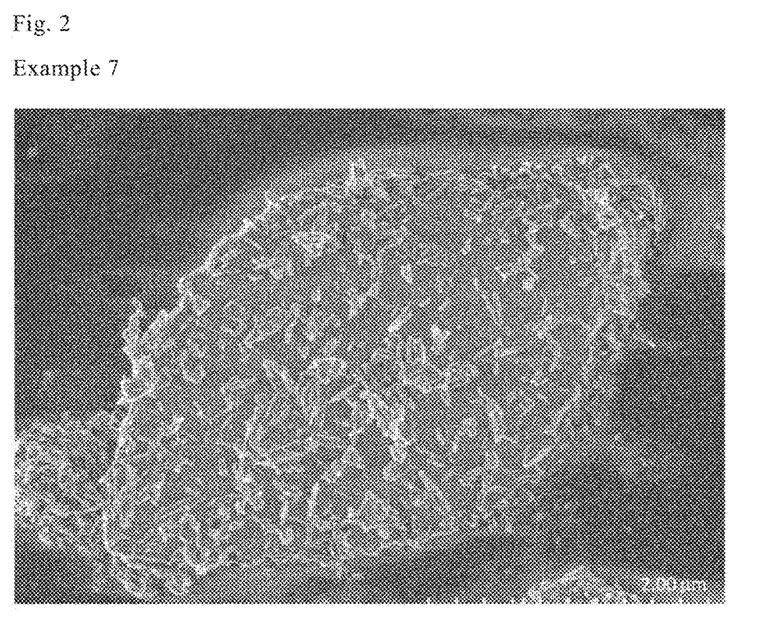
FIG. 2 is a photograph showing the result of observation of the shape of the anhydrous dibasic calcium phosphate particles obtained in Example 7.
Figure 4:
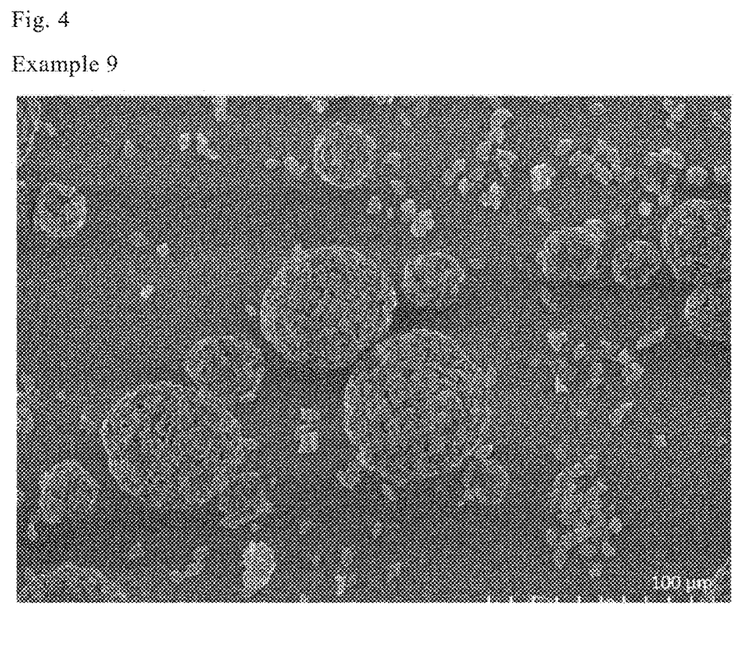
FIG. 4 is a photograph showing the result of observation of the shape of the anhydrous dibasic calcium phosphate powder obtained in Example 9.
Figure 5:
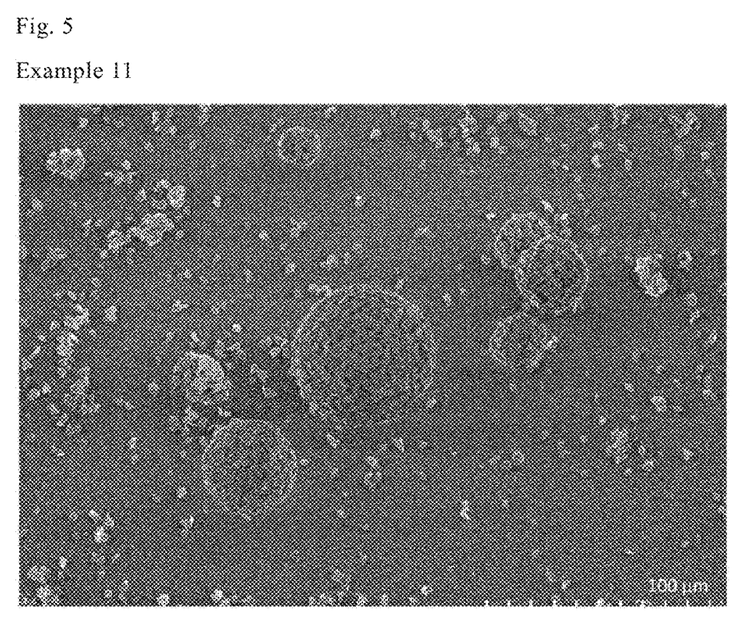
FIG. 5 is a photograph showing the result of observation of the shape of the anhydrous dibasic calcium phosphate powder obtained in Example 11.
Figure 6:
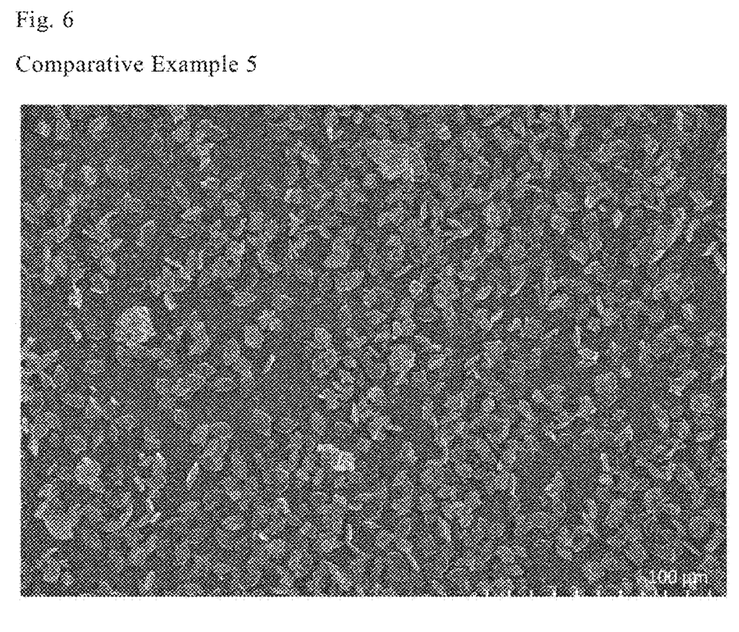
FIG. 6 is a photograph showing the result of observation of the shape of the anhydrous dibasic calcium phosphate powder obtained in Comparative Example 5.
Figure 7:
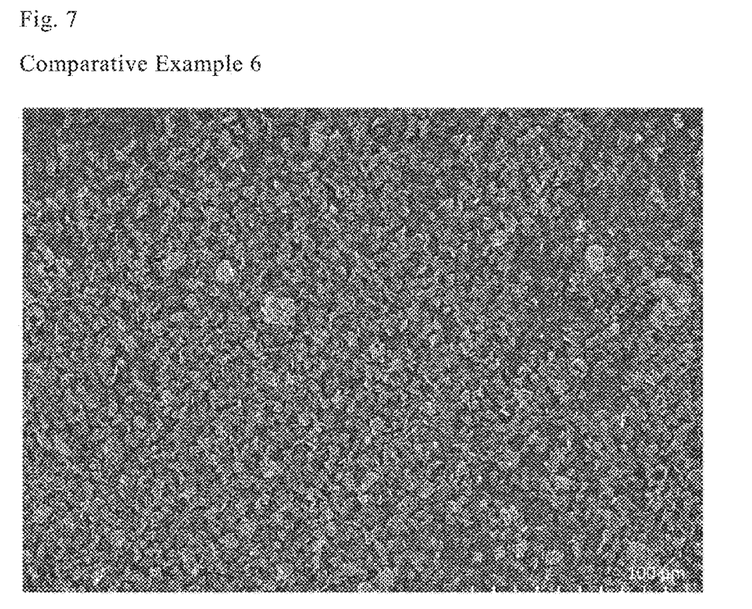
FIG. 7 is a photograph showing the result of observation of the shape of the anhydrous dibasic calcium phosphate powder obtained in Comparative Example 6.

As used herein, the term "anhydrous dibasic calcium phosphate particles" refers to a particulate polycrystal formed of an assembly of single crystals of anhydrous dibasic calcium phosphate (single crystals of about 950 angstroms as calculated based on the half-width measured using an X-ray powder diffractometer). When the anhydrous dibasic calcium phosphate particles of the present invention are observed with a field emission scanning electron microscope, particles having the external appearance as shown in FIG. 2, for example, are seen. On the other hand, as used herein, the term "anhydrous dibasic calcium phosphate powder" refers to a powder formed of agglomerated particles in which the anhydrous dibasic calcium phosphate particles are agglomerated. When the anhydrous dibasic calcium phosphate powder of the present invention is observed with a field emission scanning electron microscope, agglomerated particles having the external appearance as shown in FIG. 4, for example, are seen. The anhydrous dibasic calcium phosphate particles and the anhydrous dibasic calcium phosphate powder of the present invention will be hereinafter described in detail.

1. Anhydrous Dibasic Calcium Phosphate Particles

The anhydrous dibasic calcium phosphate particles of the present invention are characterized by having a ratio of modal pore diameter to mean particle diameter of 0.2 to 0.34, as determined by a mercury porosimeter. When the anhydrous dibasic calcium phosphate particles of the present invention are agglomerated into agglomerated particles, they can form an anhydrous dibasic calcium phosphate powder having good powder flowability and good dispersibility in a liquid. The anhydrous dibasic calcium phosphate particles of the present invention will be hereinafter described in detail.

[Physical Properties]

The anhydrous dibasic calcium phosphate particles of the present invention have a ratio of modal pore diameter to mean particle diameter of 0.2 to 0.34. Because the ratio of modal pore diameter to mean particle diameter is in this range, when the anhydrous dibasic calcium phosphate particles of the present invention form agglomerated particles, they can have good powder flowability, and despite being agglomerated particles, they can easily disintegrate and exhibit good dispersibility in a liquid. From the viewpoint of forming agglomerated particles having even better powder flowability and even better dispersibility in a liquid, the ratio of modal pore diameter to mean particle diameter is preferably 0.2 to 0.33, more preferably 0.2 to 0.30, and particularly preferably 0.23 to 0.30.

As used herein, the term "mean particle diameter" of the anhydrous dibasic calcium phosphate particles refers to the median diameter measured by laser diffractometry. Specifically, the mean particle diameter of the anhydrous dibasic calcium phosphate particles can be determined by adding a measurement sample to water and subjecting the sample to ultrasonic dispersion for 3 minutes at an ultrasonic power of 40 W, and then measuring the median diameter using laser diffractometry.

Moreover, as used herein, the term "modal pore diameter" of the anhydrous dibasic calcium phosphate particles refers to the pore size (pore diameter) at the maximum peak in a pore distribution determined by a mercury porosimeter. Specifically, the modal pore diameter of the anhydrous dibasic calcium phosphate particles can be determined by accurately weighing out 0.05 g of a measurement sample and sealing the sample into a measurement cell, determining a pore distribution based on an adsorption isotherm obtained at a mercury contact angle of 140° and a mercury surface tension of 480 dyn/cm, and specifying a pore size corresponding to the maximum peak based on the pore distribution. In general, the pore size of anhydrous dibasic calcium phosphate particles is distributed in the range of 5 to 5000 nm. In the present invention, therefore, the modal pore diameter of the anhydrous dibasic calcium phosphate particles is determined as the maximum peak in the range of pore sizes of 5 to 5000 nm.

The mean particle diameter of the anhydrous dibasic calcium phosphate particles of the present invention is not particularly limited as long as the ratio of modal pore diameter to mean particle diameter is set in the above-described range; for example, it is 1 µm or more and less than 10 µm, preferably 2 to 9 µm, and more preferably 3 to 8 µm.

The modal pore diameter of the anhydrous dibasic calcium phosphate particles of the present invention is not particularly limited as long as the ratio of modal pore diameter to mean particle diameter is set in the above-described range; for example, it is 500 to 2400 nm, preferably 700 to 2200 nm, and more preferably 900 to 2000 nm.

The static bulk specific volume of the anhydrous dibasic calcium phosphate particles of the present invention is, for example, 40 mL/10 g or less, preferably 20 to 40 mL/10 g, and more preferably 20 to 35 mL/10 g, although not particularly limited thereto. When the static bulk specific volume is in this range, there is the advantage of inhibiting dusting during production, or achieving a reduction in package size, which leads to savings in transport costs.

In the present invention, the static bulk specific volume of the anhydrous dibasic calcium phosphate particles is determined by weighing out 10.0 g of a measurement sample, slowly placing the sample into a 50-mL graduated cylinder (inner diameter: 2.0 cm), and measuring the volume (mL) of the sample. The measured volume of the sample represents the static bulk specific volume (mL/10.0 g).

One feature of the anhydrous dibasic calcium phosphate particles of the present invention is a high dibasic calcium phosphate content. The dibasic calcium phosphate content in the anhydrous dibasic calcium phosphate particles of the present invention is 97% or more, referably 98% or more, and more preferably 99% or more.

In the present invention, the dibasic calcium phosphate content in the anhydrous dibasic calcium phosphate particles is a value measured based on the analytical method for calcium monohydrogen phosphate listed in Japan's Specifications and Standards for Food Additives, 8th edition (The Ministry of Health, Labor and Welfare, Japan), and detailed measurement conditions therefor are as described in the Examples section.

[Shape]

Figure 1:
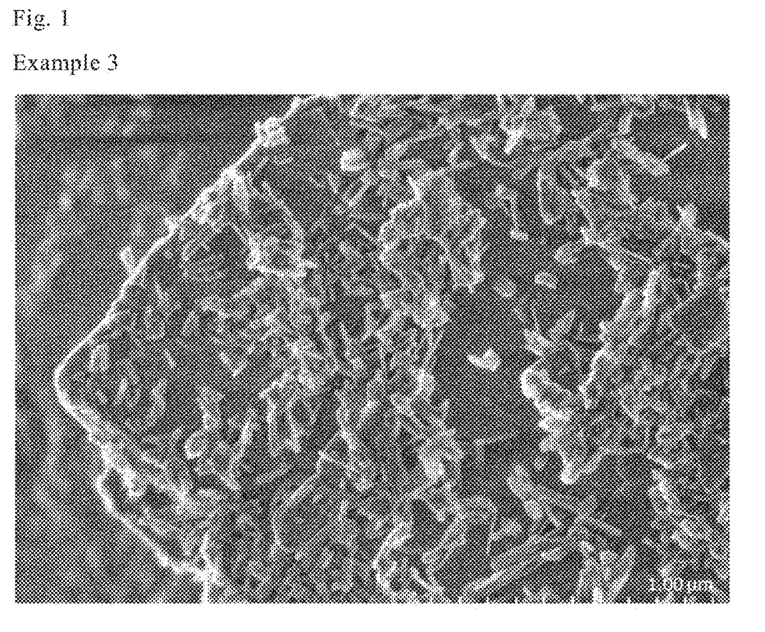
FIG. 1 is a photograph showing the result of observation of the shape of the anhydrous dibasic calcium phosphate particles obtained in Example 3.

The anhydrous dibasic calcium phosphate particles of the present invention have a characteristic shape in which many crystalline protrusions adhere to the particle surface, as shown in FIGS. 1 and 2. Because many crystalline protrusions thus adhere to the particle surface, the ratio of modal pore diameter to mean particle diameter can be set in the above-described range. Moreover, because the anhydrous dibasic calcium phosphate particles of the present invention have this characteristic shape, when they are agglomerated, they can form, for example, spherical agglomerated particles, and the agglomerated particles can be imparted with excellent flowability, as well as good dispersibility in a liquid, despite being composed of agglomerated particles.

APPLICATIONS

The anhydrous dibasic calcium phosphate particles of the present invention are used as various additives or ingredients for food products, cosmetic preparations, pharmaceuticals, and the like. The anhydrous dibasic calcium phosphate particles of the present invention may be used as they are, without being agglomerated, as various additives or ingredients, or may be agglomerated to form agglomerated particles and used as various additives or ingredients, as described below. In particular, the powder composed of the agglomerated particles formed by agglomerating the anhydrous dibasic calcium phosphate particles of the present invention has the advantage of exhibiting good flowability in powdery form and good dispersibility in a liquid, and being easy to handle.

[Production Method]

Specific examples of the method for producing the anhydrous dibasic calcium phosphate particles of the present invention include, although not particularly limited to, a method including the following first to third steps. Each of the steps of the method for producing the anhydrous dibasic calcium phosphate particles of the present invention will be hereinafter described:

(a) a first step of preparing a calcium hydroxide-containing solution, wherein the calcium hydroxide-containing solution contains calcium hydroxide and calcium ions, and a molar ratio of calcium atoms present as the calcium ions, relative to calcium atoms constituting the calcium hydroxide, is 0.04 to 0.16;

(b) a second step of adding phosphoric acid to the calcium hydroxide-containing solution obtained in the first step to obtain a first dibasic calcium phosphate-containing solution; and (c) a third step of adding an alkali metal hydroxide to the first dibasic calcium phosphate-containing solution obtained in the second step, wherein the amount of the alkali metal hydroxide to be added is adjusted to 1.5 to 13.0 mol per mole of the calcium atoms present as the calcium ions in the calcium hydroxide-containing solution prepared in the first step, to obtain a second dibasic calcium phosphate-containing solution.

First Step

In the first step, a calcium hydroxide-containing solution is prepared, which contains calcium hydroxide and calcium ions, and in which a molar ratio of calcium atoms present as the calcium ions, relative to calcium atoms constituting the calcium hydroxide, is 0.04 to 0.16.

In the calcium hydroxide-containing solution prepared in the first step, the molar ratio of calcium atoms present as the calcium ions, relative to calcium atoms constituting the calcium hydroxide, is preferably 0.05 to 0.15, and more preferably 0.06 to 0.14.

The calcium hydroxide content in the calcium hydroxide-containing solution prepared in the first step is, for example, 1 to 20% by weight, preferably 3 to 18% by weight, and more preferably 5 to 15% by weight, although not particularly limited thereto.

The method for preparing the calcium hydroxide-containing solution having the above-described specific composition in the first step is not particularly limited, and the calcium hydroxide-containing solution can be prepared in accordance with a technique known in the art. Examples of the method include a method in which a soluble calcium salt and an alkali metal hydroxide are allowed to coexist at a specific molar ratio in water; a method in which a calcium hydroxide is added into water, and then a water-soluble calcium salt is added to give the above-described composition: and a method in which calcium oxide and/or calcium hydroxide is added into water, and a predetermined amount of an acid solvent is added to give the above-described composition.

The method for performing the first step by allowing a soluble calcium salt and an alkali metal hydroxide to coexist at a specific molar ratio in water will be hereinafter described in detail.

In the first step, in order to obtain the calcium hydroxide-containing solution having the above-described specific composition by allowing a soluble calcium salt and an alkali metal hydroxide to coexist at a specific molar ratio in water, specifically, the soluble calcium salt and the alkali metal hydroxide may be allowed to coexist in water such that a molar ratio of alkali metal atoms relative to calcium atoms becomes 1.73 to 1.91. When the soluble calcium salt and the alkali metal hydroxide are allowed to coexist and reacted in water, calcium hydroxide is formed from the soluble calcium salt. For example, when X mol of the soluble calcium salt calculated as calcium atoms and Y mol of the alkali metal hydroxide calculated as alkali metal atoms is allowed to coexist in water, Y/2 mol of calcium hydroxide is produced, and a calcium hydroxide-containing solution is obtained in which X-(Y/2) mol of calcium ions has been released.

While the soluble calcium salt is not particularly limited as long as it is a calcium salt that can dissolve in water or an aqueous acid solution, examples include inorganic acid salts, such as calcium chloride and calcium nitrate; and organic acid salts, such as calcium acetate, calcium lactate, calcium citrate, calcium succinate, calcium gluconate, and calcium fumarate. The soluble calcium salt may also be a soluble calcium salt formed by dissolving an insoluble calcium salt, such as calcium carbonate, calcium oxide, calcium hydroxide, calcium sulfate, or calcium silicate, in an acid solvent, such as hydrochloric acid. These soluble calcium salts may be used alone or in combinations of two or more. Among these soluble calcium salts, calcium chloride is preferred.

Examples of the alkali metal hydroxide include, although not particularly limited to, sodium hydroxide and potassium hydroxide. These alkali metal hydroxides may be used alone or in combinations of two or more. Among these alkali metal hydroxides, sodium hydroxide is preferred.

While the amount of the soluble calcium salt to be used is not particularly limited, for example, it may be adjusted such that the concentration of the soluble calcium salt in water at the start of reaction is 5 to 50% by weight, preferably 10 to 40% by weight, and more preferably 20 to 30% by weight.

The amount of the alkali metal hydroxide to be used may be adjusted in the range of amounts such that the molar ratio of alkali metal atoms relative to calcium atoms constituting the soluble calcium salt to be used becomes 1.73 to 1.91; preferably, it is 1.76 to 1.88, and more preferably 1.79 to 1.85. When the soluble calcium salt and the alkali metal hydroxide are allowed to coexist to give such a molar ratio, a calcium hydroxide-containing solution can be obtained in which the molar ratio of calcium atoms present as the calcium ions, relative to calcium atoms constituting the calcium hydroxide, is set in the above-described range.

The temperature during which the soluble calcium salt and the alkali metal hydroxide are allowed to coexist may be appropriately adjusted according to the amount of the soluble calcium salt to be added and the like; for example, it is 20 to 60° C., preferably 30 to 50° C., and more preferably 35 to 45° C.

In the first step, the soluble calcium salt and the alkali metal hydroxide may be allowed to coexist in a dissolved state in water. Suitable examples of the method therefor include a method in which an aqueous solution of the soluble calcium salt is prepared, and then a predetermined amount of an aqueous solution of the alkali metal hydroxide is added dropwise to the aqueous solution of the soluble calcium salt, and the mixture is stirred.

Calcium hydroxide is produced by allowing the soluble calcium salt and the alkali metal hydroxide to coexist; in order to efficiently produce the calcium hydroxide, it is preferred that, after the soluble calcium salt and the alkali metal hydroxide are allowed to coexist, aging be performed at the above-described temperature. As used herein, the term "aging" refers to allowing to stand or stand with stirring for a certain time.

While the aging time in the first step may be appropriately adjusted according to the amount of the soluble calcium salt to be added, the reaction temperature, and the like, it is, for example, 10 minutes or more, preferably 10 to 120 minutes, and more preferably 30 to 90 minutes. As used herein, the term "aging time" refers to the time during which the soluble calcium salt and the alkali metal hydroxide are allowed to stand or stand with stirring, starting from zero minute, defined as the time point at which the entire amount of the soluble calcium salt and the alkali metal hydroxide has been allowed to coexist in water. For example, in the case where an aqueous solution of the alkali metal hydroxide is added dropwise to an aqueous solution of the soluble calcium salt, the aging time is the time calculated from zero minute, defined as the time point at which the dropwise addition of the aqueous solution of the alkali metal hydroxide has been completed.

While the thus-obtained calcium hydroxide-containing solution can be directly subjected to the second step, it may be optionally diluted with water, or concentrated by evaporating the water, before being subjected to the second step.

Second Step

In the second step, phosphoric acid is added to the calcium hydroxide-containing solution obtained in the first step to obtain a first dibasic calcium phosphate-containing solution.

In the second step, phosphoric acid ($H_3PO_4$) may be added as is, or in the form of an aqueous solution.

The amount of phosphoric acid to be added may be appropriately adjusted in the range of amounts where dibasic calcium phosphate is produced; for example, it may be adjusted such that the molar ratio of phosphoric acid relative to total calcium atoms contained in the calcium hydroxide-containing solution becomes 0.85 to 1.05, preferably 0.90 to 1.00, and more preferably 0.93 to 0.97. As used herein, the phrase "total calcium atoms contained in the calcium hydroxide-containing solution" refers to the sum total of calcium atoms constituting the calcium hydroxide and calcium atoms constituting the calcium ions contained in the calcium hydroxide-containing solution.

The temperature during which phosphoric acid is added to the calcium hydroxide-containing solution may be appropriately adjusted according to the amount of the calcium hydroxide-containing solution, the amount of phosphoric acid to be added, and the like; for example, it is 20 to 60° C., preferably 30 to 50° C., and more preferably 35 to 45° C.

Suitable examples of the method for adding phosphoric acid to the calcium hydroxide-containing solution include, although not particularly limited to, a method in which a predetermined amount of phosphoric acid is added dropwise to the calcium hydroxide-containing solution, and the mixture is stirred.

First dibasic calcium phosphate is produced by adding phosphoric acid to the calcium hydroxide-containing solution; in order to efficiently produce the first dibasic calcium phosphate, it is preferred that, after phosphoric acid is added to the calcium hydroxide-containing solution, aging be performed at the above-described temperature.

While the aging time in the second step may be appropriately adjusted according to the amount of the calcium hydroxide-containing solution, the amount of phosphoric acid to be added, and the like, it is, for example, 10 minutes or more, preferably 10 to 120 minutes, and more preferably 30 to 90 minutes. As used herein, the term "aging time" refers to the time during which the calcium hydroxide-containing solution and phosphoric acid are allowed to stand or stand with stirring, starting from zero minute, defined as the time point at which the entire amount of phosphoric acid has been added to the calcium hydroxide-containing solution. For example, in the case where phosphoric acid is added dropwise to the calcium hydroxide-containing solution, the aging time is the time calculated from zero minute, defined as the time point at which the dropwise addition of phosphoric acid has been completed.

The thus-obtained first dibasic calcium phosphate-containing solution is in the form of a suspension in which dibasic calcium phosphate is suspended. While the calcium hydroxide-containing solution obtained in the second step can be directly subjected to the third step, it may be optionally diluted with water, or concentrated by evaporating the water, before being subjected to the third step.

Third Step

The third step is the step of adding an alkali metal hydroxide or an aqueous solution containing the alkali metal hydroxide to the first dibasic calcium phosphate-containing solution obtained in the second step, wherein the amount of the alkali metal hydroxide to be added is adjusted to 1.5 to 13.0 mol per mole of the calcium atoms present as the calcium ions in the calcium hydroxide-containing solution prepared in the first step, to thereby obtain a second dibasic calcium phosphate-containing solution.

Examples of the alkali metal hydroxide to be used in the third step are the same as those mentioned in the first step. The alkali metal hydroxide to be used in the third step is preferably sodium hydroxide. In the third step, the alkali metal hydroxide may be added as is, but is preferably added in the form of an aqueous solution containing the alkali metal hydroxide.

The amount of the alkali metal hydroxide to be added is adjusted to 1.5 to 13.0 mol per mole of the calcium atoms present as the calcium ions in the calcium hydroxide-containing solution prepared in the first step. The amount of the alkali metal hydroxide to be added is preferably 1.6 to 10.0 mol, more preferably 1.6 to 5.0 mol, and particularly preferably 1.6 to 3.0 mol, per mole of the calcium atoms present as the calcium ions in the calcium hydroxide-containing solution prepared in the first step.

More specifically, in the case where the calcium hydroxide-containing solution is prepared in the first step by allowing the soluble calcium salt and the alkali metal hydroxide to coexist in water such that the molar ratio of alkali metal atoms relative to calcium atoms becomes 1.73 to 1.91, the amount of the alkali metal hydroxide to be added in the third step may be adjusted such that the molar ratio of alkali metal atoms relative to calcium atoms in the solution becomes 1.95 to 2.5. As used herein, the phrase "molar ratio of alkali metal atoms relative to calcium atoms in the solution" refers to the ratio of the total number of moles of alkali metal atoms derived from the alkali metal hydroxide used in the first and third steps, relative to the total number of moles of calcium atoms contained in the calcium-containing solution prepared in the first step (the total number of moles of calcium atoms constituting the calcium hydroxide and calcium atoms constituting the calcium ions contained in the solution). In this case, the amount of the alkali metal hydroxide to be added is preferably such that the above-described molar ratio becomes 1.95 to 2.5, and more preferably 1.98 to 2.10. When the molar ratio is set in this range, the amount of the alkali metal hydroxide added can be adjusted to 1.5 to 13.0 mol per mole of the calcium atoms present as the calcium ions in the calcium hydroxide-containing solution prepared in the first step.

In the third step, substances other than the alkali metal hydroxide may be added to the first dibasic calcium phosphate-containing solution, as long as they do not hinder the production of the anhydrous dibasic calcium phosphate of the present invention.

The temperature during which the alkali metal hydroxide is added to the first dibasic calcium phosphate-containing solution may be appropriately adjusted according to the amount of the first dibasic calcium phosphate-containing solution, the amount of the alkali metal hydroxide to be added, and the like; for example, it is 20 to 60° C. preferably 30 to 50° C., and more preferably 35 to 45° C.

The target second dibasic calcium phosphate is produced as a suspension by adding the above-described amount of the alkali metal hydroxide to the first dibasic calcium phosphate-containing solution; in order to efficiently produce the anhydrous dibasic calcium phosphate, it is preferred that aging be performed by appropriately adjusting the temperature. The temperature during the aging is, for example, 60 to 100° C., and preferably 80 to 100° C.

While the aging time in the third step may be appropriately adjusted by confirming that the target anhydrous dibasic calcium phosphate has produced, it is, for example, 60 minutes or more, preferably 60 to 240 minutes, and more preferably 120 to 180 minutes. As used herein, the term "aging time" refers to the time during which the first dibasic calcium phosphate-containing solution and the alkali metal hydroxide are allowed to stand or stand with stirring, starting from zero minute, defined as the time point at which the entire amount of the alkali metal hydroxide has been added to the first dibasic calcium phosphate-containing solution. For example, in the case where an aqueous solution of the alkali metal hydroxide is added dropwise to the first dibasic calcium phosphate-containing solution, the aging time is the time calculated from zero minute, defined as the time point at which the dropwise addition of the aqueous solution of the alkali metal hydroxide has been completed.

In the first to third steps, or after the third step, a PH adjuster may be separately added. Examples of usable pH adjusters include, although not particularly limited to, liquid acids, such as hydrochloric acid, lactic acid, and gluconic acid; solid acids, such as citric acid, succinic acid, fumaric acid, malic acid, and glucono-delta-lactone; and sodium salts, potassium salts, calcium salts, magnesium salts, and the like thereof. Examples of alkalis include sodium hydroxide and potassium hydroxide.

The thus-obtained second dibasic calcium phosphate-containing solution contains the anhydrous dibasic calcium phosphate particles of the present invention in a dispersed state.

The anhydrous dibasic calcium phosphate particles of the present invention are obtained by subjecting the second dibasic calcium phosphate-containing solution to a solid-liquid separation treatment, such as filtration, and collecting solids, optionally washing the solids with water, and then subjecting the solids to a drying treatment.

The drying treatment for the solids collected from the second dibasic calcium phosphate-containing solution may be performed by any of shelf drying, hot-air drying, spray drying, freeze drying, fluidized-bed drying, and the like. When the second dibasic calcium phosphate-containing solution is subjected to the drying treatment, the resulting product is in a state where the anhydrous dibasic calcium phosphate particles of the present invention are agglomerated to form agglomerated particles. Thus, in order to obtain the anhydrous dibasic calcium phosphate particles of the present invention (in the state of non-agglomerated particles), the agglomerated particles, after the drying treatment, may be subjected to a dispersion treatment or the like to disintegrate the agglomerated state.

2. Anhydrous Dibasic Calcium Phosphate Powder

The anhydrous dibasic calcium phosphate powder of the present invention is characterized by comprising agglomerated particles in which the anhydrous dibasic calcium phosphate particles are agglomerated. The anhydrous dibasic calcium phosphate particles, when they are agglomerated, form spherical particles, for example; however, the agglomerated particles have weak cohesion, and have a property such that the agglomerated state is easily loosened by a stirring treatment, an ultrasonic treatment, or the like in water, and turns into a minutely dispersed state. Therefore, the anhydrous dibasic calcium phosphate powder of the present invention formed of the agglomerated particles in which the anhydrous dibasic calcium phosphate particles are agglomerated has the advantage of having good flowability in powdery state, and despite being agglomerated particles, having good dispersibility by being easily loosened into the anhydrous dibasic calcium phosphate particles in water, and being easy to handle in the production of various products containing dibasic calcium phosphate.

[Physical Properties]

In one preferred embodiment, the anhydrous dibasic calcium phosphate powder of the present invention has an angle of repose of 45° or less, preferably 25 to 45°, and more preferably 25 to 40°. The angle of repose is an index of the flowability of a powder; a smaller value of the angle of repose means that a powder with an angle of repose of 45° or less has higher flowability that allows easy handing in the production of various products.

In the present invention, the angle of repose of the anhydrous dibasic calcium phosphate powder is determined as follows: a measurement sample is slowly dropped onto a dish having a diameter of 50 mm, from a position at a height of 100 mm, and at the time when a height from the bottom of the dish to the top of the anhydrous dibasic calcium phosphate powder has stabilized, the height is measured, and the angle of repose is calculated in accordance with the following equation:

$$\text{angle of repose (°)} = \tan^{-1} (\text{height to the top of the anhydrous dibasic calcium phosphate powder} / \text{radius of the dish (25 mm)}) \quad \text{[Expression 1]}$$

While the particle diameter of the agglomerated particles constituting the anhydrous dibasic calcium phosphate powder of the present invention is not particularly limited, it is, for example, 10 to 120 µm, preferably 20 to 110 µm, and more preferably 30 to 100 µm. The particle diameter of the agglomerated particles is determined by observing 100 or more agglomerated particles with a microscope, and calculating the average value of the diameters.

[Applications]

The anhydrous dibasic calcium phosphate powder of the present invention is used as various additives or ingredients for food products, cosmetic preparations, pharmaceuticals, and the like. Moreover, the anhydrous dibasic calcium phosphate powder of the present invention can be optionally subjected to a treatment such as grinding, and then provided or used.

[Production Method]

The anhydrous dibasic calcium phosphate powder of the present invention can be produced by forming agglomerated particles by agglomerating the anhydrous dibasic calcium phosphate particles. To form the agglomerated particles of the anhydrous dibasic calcium phosphate particles, for example, an aqueous solution in which the anhydrous dibasic calcium phosphate particles are suspended may be subjected to a drying treatment.

Specific examples of the method for producing the anhydrous dibasic calcium phosphate powder of the present invention include a method in which the anhydrous dibasic calcium phosphate particles are dispersed in water and subjected to a drying treatment, such as spray drying and a method in which the solids collected from the second dibasic calcium phosphate-containing solution obtained in the third step of the method for producing the anhydrous dibasic calcium phosphate particles are formed into a suspension, and then subjected to a drying treatment, such as shelf drying, hot-air drying, spray drying, freeze drying, or fluidized-bed drying.

EXAMPLES

The present invention will be hereinafter described in more detail based on examples, although the present invention is not limited thereto.

Test Example 1

Production of Anhydrous Dibasic Calcium Phosphate Particles and Evaluation of Physical Properties 1. Production of Anhydrous Dibasic Calcium Phosphate Particles Example 1

(First Step)

1800 mL of water was weighed out into a 5-L container, 633 g of granular calcium chloride was added thereto, and the mixture was stirred at 240 rpm to prepare a calcium chloride solution. The calcium chloride solution was warmed to 40° C., and a 48% by weight aqueous solution of sodium hydroxide was added thereto over 1 hour such that the molar ratio of sodium atoms/calcium atoms became 1.82; thereafter, the mixture was stirred for 30 minutes while maintaining the temperature at 40° C., to obtain a calcium hydroxide-containing solution.

(Second Step)

472 g of an 85% by weight aqueous solution of phosphoric acid was adjusted to 733 g by adding water, and the aqueous solution of phosphoric acid was added dropwise to the calcium hydroxide-containing solution warmed to 40° C. over 4 hours. After the dropwise addition was completed, the mixture was stirred for 1 hour while maintaining the temperature at 40° C., to obtain a first dibasic calcium phosphate-containing solution.

(Third Step)

To the first dibasic calcium phosphate-containing solution being warmed at 40° C. a 48% by weight aqueous solution of sodium hydroxide was added such that the molar ratio of sodium atoms/calcium atoms in the solution became 1.98, and the mixture was further subjected to aging while stirring at 90° C. for 3 hours, to obtain a second dibasic calcium phosphate-containing solution. Subsequently, the second dibasic calcium phosphate-containing solution was cooled, and then filtered and dehydrated, and washed with water. The resulting reaction product (solid matter) was placed in a shelf dryer and dried at 105° C. for 16 hours, and the dried product was disintegrated in a desktop mill to obtain anhydrous dibasic calcium phosphate particles.

Example 2

Anhydrous dibasic calcium phosphate particles were obtained by performing the same procedure as that of Example 1, except that in the third step, a 48% by weight aqueous solution of sodium hydroxide was added to the first dibasic calcium phosphate-containing solution such that the molar ratio of sodium atoms/calcium atoms in the solution became 1.99.

Example 3

Anhydrous dibasic calcium phosphate particles were obtained by performing the same procedure as that of Example 1, except that in the third step, a 48% by weight aqueous solution of sodium hydroxide was added to the first dibasic calcium phosphate-containing solution such that the molar ratio of sodium atoms/calcium atoms in the solution became 2.00.

Example 4

Anhydrous dibasic calcium phosphate particles were obtained by performing the same procedure as that of Example 1, except that in the third step, a 48% by weight aqueous solution of sodium hydroxide was added to the first dibasic calcium phosphate-containing solution such that the molar ratio of sodium atoms/calcium atoms in the solution became 2.03.

Example 5

Anhydrous dibasic calcium phosphate particles were obtained by performing the same procedure as that of Example 1, except that in the third step, a 48% by weight aqueous solution of sodium hydroxide was added to the first dibasic calcium phosphate-containing solution such that the molar ratio of sodium atoms/calcium atoms in the solution became 2.05.

Example 6

Anhydrous dibasic calcium phosphate particles were obtained by performing the same procedure as that of Example 1, except that in the third step, a 48% by weight aqueous solution of sodium hydroxide was added to the first dibasic calcium phosphate-containing solution such that the molar ratio of sodium atoms/calcium atoms in the solution became 2.07.

Example 7

(First Step)

2700 L of water was weighed out into a 7-t container, 950 kg of granular calcium chloride was added thereto, and the mixture was stirred to prepare a calcium chloride solution. The calcium chloride solution was warmed to 40° C., and a 48% by weight aqueous solution of sodium hydroxide was added thereto over 1 hour such that the molar ratio of sodium atoms/calcium atoms became 1.82; thereafter, the mixture was stirred for 30 minutes while maintaining the temperature at 40° C. to obtain a calcium hydroxide-containing solution.

(Second Step)

708 kg of an 85% by weight aqueous solution of phosphoric acid was adjusted to 1100 kg by adding water, and the aqueous solution of phosphoric acid was added dropwise to the calcium hydroxide-containing solution warmed to 40° C. over 4 hours. The mixture was stirred for 1 hour while maintaining the temperature at 40° C., to obtain a first dibasic calcium phosphate-containing solution.

(Third Step)

To the first dibasic calcium phosphate-containing solution being warmed at 40° C., a 48% by weight aqueous solution of sodium hydroxide was added such that the molar ratio of sodium atoms/calcium atoms in the solution became 2.00, and the mixture was further subjected to aging while stirring at 90° C. for 3 hours, to obtain a second dibasic calcium phosphate-containing solution. Subsequently, the second dibasic calcium phosphate-containing solution was cooled, and then filtered and dehydrated, and washed with water. A portion of the resulting reaction product (solid matter) was collected, placed in a shelf dryer, and dried at 105° C. for 16 hours, and the dried product was disintegrated in a desktop mill to obtain anhydrous dibasic calcium phosphate particles.

Comparative Example 1

(First Step)

1800 mL of water was weighed out into a 5-L container, 633 g of granular calcium chloride was added thereto, and the mixture was stirred at 240 rpm to prepare a calcium chloride solution. The calcium chloride solution was warmed to 40° C., and a 48% by weight aqueous solution of sodium hydroxide was added thereto over 1 hour such that the molar ratio of sodium atoms/calcium atoms became 1.82; thereafter, the mixture was stirred for 30 minutes while maintaining the temperature at 40° C., to obtain a calcium hydroxide-containing solution.

(Second Step)

472 g of an 85% by weight aqueous solution of phosphoric acid was adjusted to 733 g by adding water, and the aqueous solution of phosphoric acid was added dropwise to the calcium hydroxide-containing solution warmed to 40° C. over 4 hours. After the dropwise addition was completed, the mixture was stirred for 1 hour while maintaining the temperature at 40° C., and further subjected to aging while stirring at 90° C. for 3 hours, to obtain a first dibasic calcium phosphate-containing solution.

The first dibasic calcium phosphate-containing solution was cooled, and then filtered and dehydrated, and washed with water. The resulting reaction product (solid matter) was placed in a shelf dryer and dried at 105° C. for 16 hours, and the dried product was disintegrated in a desktop mill to obtain anhydrous dibasic calcium phosphate particles.

Comparative Example 2

(First Step and Second Step)

A first dibasic calcium phosphate-containing solution was obtained by performing the first step and the second step under the same conditions as those in Comparative Example 1 above.

(Third Step)

To the first dibasic calcium phosphate-containing solution being warmed at 40° C. a 48% by weight aqueous solution of sodium hydroxide was added such that the molar ratio of sodium atoms/calcium atoms became 1.89, and the mixture was further subjected to aging while stirring at 90° C. for 3 hours, to obtain a second dibasic calcium phosphate-containing solution. Subsequently, the second dibasic calcium phosphate-containing solution was cooled, and then filtered and dehydrated, and washed with water. The resulting reaction product (solid matter) was placed in a shelf dryer and dried at 105° C. for 16 hours, and the dried product was disintegrated in a desktop mill to obtain anhydrous dibasic calcium phosphate particles.

Comparative Example 3

Anhydrous dibasic calcium phosphate particles were obtained by performing the same procedure as that of Comparative Example 2, except that in the third step, a 48% by weight aqueous solution of sodium hydroxide was added to the first dibasic calcium phosphate-containing solution such that the molar ratio of sodium atoms/calcium atoms became 1.91.

Comparative Example 4

(First Step)

2700 L of water was weighed out into a. 7-t container, 950 kg of granular calcium chloride was added thereto, and the mixture was stirred to prepare a calcium chloride solution. The calcium chloride solution was warmed to 40° C., and a 48% by weight aqueous solution of sodium hydroxide was added thereto over 1 hour such that the molar ratio of sodium atoms/calcium atoms became 1.82; thereafter, the mixture was stirred for 30 minutes while maintaining the temperature at 40° C., to obtain a calcium hydroxide-containing solution.

(Second Step)

708 kg of an 85% by weight aqueous solution of phosphoric acid was adjusted to 1100 kg by adding water, and the aqueous solution of phosphoric acid was added dropwise to the calcium hydroxide-containing solution over 4 hours. After the dropwise addition was completed, the mixture was stirred for 1 hour while maintaining the temperature at 40° C., to obtain a first dibasic calcium phosphate-containing solution.

(Third Step)

To the first dibasic calcium phosphate-containing solution being warmed at 40° C., a 48% by weight aqueous solution of sodium hydroxide was added such that the molar ratio of sodium atoms/calcium atoms in the solution became 1.91, and the mixture was subjected to aging while stirring at 90° C. for 3 hours, to obtain a second dibasic calcium phosphate-containing solution. Subsequently, the second dibasic calcium phosphate-containing solution was cooled, and then filtered and dehydrated, and washed with water. A portion of the resulting reaction product (solid matter) was collected, placed in a shelf dryer, and dried at 105° C. for 16 hours, and the dried product was disintegrated in a desktop mill to obtain anhydrous dibasic calcium phosphate particles.

2. Methods for Evaluating Physical Properties

For the anhydrous dibasic calcium phosphate particles obtained in Examples 1 to 7 and Comparative Examples 1 to 4, the modal pore diameter, the mean particle diameter, the static bulk specific volume, the dibasic calcium phosphate content, and the shape were each measured using the following methods.

2-1. Modal Pore Diameter

The modal pore diameter was determined under the following conditions, using a mercury porosimeter ("Pore-Master 60GT" from Quantachrome Corporation).

0.05 g of the anhydrous dibasic calcium phosphate particles was accurately weighed out and sealed in a measurement cell, and an adsorption isotherm of mercury was determined under mercury intrusion, at a mercury contact angle of 140° and a mercury surface tension of 480 dyn/cm. A pore distribution was determined from the adsorption isotherm, and a pore size corresponding to the maximum peak was specified as the modal pore diameter, based on the pore distribution. The modal pore diameter was determined as the maximum peak in the range of pore sizes of 5 to 5000 nm.

2-2. Mean Particle Diameter (D50)

The anhydrous dibasic calcium phosphate particles were added into water and subjected to ultrasonic dispersion for 3 minutes (ultrasonic power 40 W), and then the median diameter was determined by laser diffractometry, using "MICROTRAC MT3300EXII" from Microtrac.

2-3. Static Bulk Specific Volume 10.0 g of the anhydrous dibasic calcium phosphate particles was weighed out and slowly placed in a 50-mL graduated cylinder (inner diameter: 2.0 cm), and the volume (mL) of the sample was measured as the static bulk specific volume (mL/10.0 g).

2-4. Dibasic Calcium Phosphate Content

The dibasic calcium phosphate content was measured based on the analytical method for calcium monohydrogen phosphate listed in Japan's Specifications and Standards for Food Additives, 8th edition (The Ministry of Health, Labor and Welfare, Japan). Specifically, the measurement was performed as follows: The anhydrous dibasic calcium phosphate particles were dried at 200° C. for 3 hours; then, about 0.4 g of the particles was precisely weighed out, and 12 mL of hydrochloric acid (1→4) was added to dissolve the particles, and the solution was accurately adjusted to 200 mL by further adding water to prepare a test solution. 20 mL of the test solution was accurately weighed out, and 25 mL of a 0.02 mol/L EDTA solution was accurately weighed out and added; subsequently, 50 mL of water and 5 mL of ammonia-ammonium chloride buffer (pH 10.7) were added, and the mixture was allowed to stand for about 1 minute; then, 0.025 g of eriochrome black T-sodium chloride indicator was added, and an excessive amount of EDTA was immediately titrated with a 0.02 mol/L zinc acetate solution. The endpoint was defined as the time at which the solution changed in color from blue to bluish purple. Separately, a blank test (the same test without adding the anhydrous dibasic calcium phosphate particles) was performed, and the dibasic calcium phosphate content was calculated in accordance with the following equation:

$$\text{dibasic calcium phosphate content (\%)} = [\{(\text{titer(mL) in the blank test} - \text{titer(mL) in the present test}) \times 2.721 \times 10\}/\text{amount(mg) of the collected sample}] \times 100 \qquad [\text{Expression 2}]$$

2-5. Shape

The particle shape of the anhydrous dibasic calcium phosphate particles was measured using a field emission scanning electron microscope ("SU8200" from Hitachi High-Technologies Corporation) at an accelerated voltage of 1 kV and an emission current of 10 μA.

3. Results of Evaluation of Physical Properties

Figure 3:
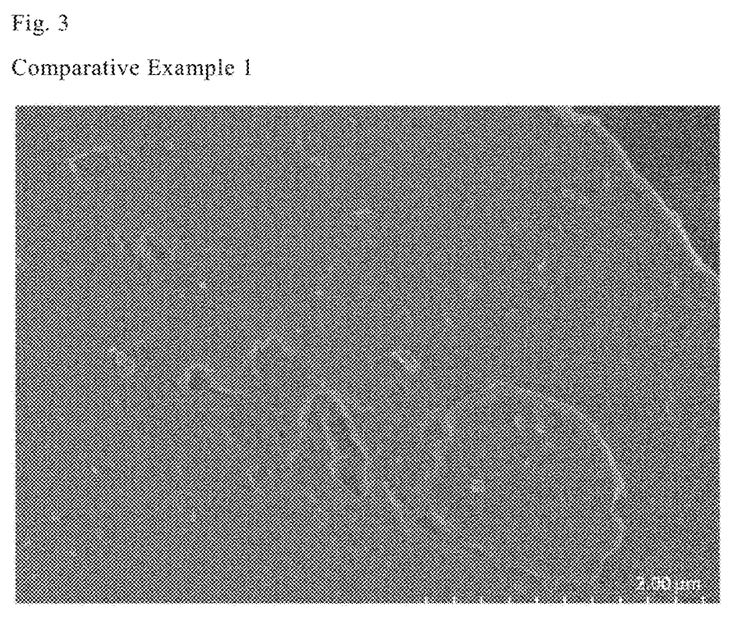
FIG. 3 is a photograph showing the result of observation of the shape of the anhydrous dibasic calcium phosphate particles obtained in Comparative Example 1.

As a result of observation of the shape of the anhydrous dibasic calcium phosphate particles of each example, the anhydrous dibasic calcium phosphate particles of Examples 1 to 7 had a shape in which many crystalline deposits adhere to the particle surface, and were clearly different in particle shape from the anhydrous dibasic calcium phosphate particles of the comparative examples, which had a relatively smooth particle surface. For reference, FIGS. 1 to 3 show the results of observation of the shapes of the anhydrous dibasic calcium phosphate particles obtained in Example 3, Example 7, and Comparative Example 1. FIG. 2 shows an image of substantially the entire particle surface, and FIGS. 1 and 3 each show an image of a portion of the particle surface.

Table 1 shows the results of measurement of the modal pore diameter, the mean particle diameter, the static bulk specific volume, and the dibasic calcium phosphate content. The anhydrous dibasic calcium phosphate particles obtained in Examples 7 had a modal pore diameter/mean particle diameter ratio in the range of 0.2 to 0.34, and had a high dibasic calcium phosphate content. i.e., 97% or more.

TABLE 1

| | First step | | | | Physical property values of the anhydrous dibasic calcium phosphate particles | |
|---|---|---|---|---|---|---|
| | Molar ratio of calcium atoms present as the calcium ions, relative to calcium atoms constituting the calcium hydroxide*1 | Molar ratio of sodium atoms/calcium atoms*2 | Third step Amount (mol) of sodium hydroxide added*3 | Molar ratio of sodium atoms to calcium atoms finally added in all the steps*4 | Modal pore Diameter (nm) | D10 (μm) |
| Example 1 | 0.10 | 1.82 | 1.80 | 1.98 | 1931 | 4.6 |
| Example 2 | 0.10 | 1.82 | 1.93 | 1.99 | 1681 | 4.0 |
| Example 3 | 0.10 | 1.82 | 2.05 | 2.00 | 1512 | 4.1 |
| Example 4 | 0.10 | 1.82 | 2.30 | 2.03 | 1476 | 4.3 |
| Example 5 | 0.10 | 1.82 | 2.55 | 2.05 | 1478 | 4.2 |
| Example 6 | 0.10 | 1.82 | 2.80 | 2.07 | 1478 | 4.2 |
| Example 7 | 0.10 | 1.82 | 2.00 | 2.00 | 917 | 2.3 |
| Comparative Example 1 | 0.10 | 1.82 | 0 | 1.82 | 2677 | 4.6 |

TABLE 1-continued

| | | | | | | |
|---|---|---|---|---|---|---|
| Comparative Example 2 | 0.10 | 1.82 | 0.80 | 1.89 | 2688 | 4.5 |
| Comparative Example 3 | 0.10 | 1.82 | 1.08 | 1.91 | 2399 | 4.8 |
| Comparative Example 4 | 0.10 | 1.82 | 1.01 | 1.91 | 1632 | 2.6 |

| | Physical property values of the anhydrous dibasic calcium phosphate particles | | | | | |
|---|---|---|---|---|---|---|
| | D50 (μm) | D90 (μm) | D95 (μm) | Modal pore diameter/mean particle diameter | Static bulk Specific Volume (mL/10 g) | Dibasic Calcium Phosphate content (%) |
| Example 1 | 6.5 | 10.0 | 11.8 | 0.30 | 21.5 | 97.9 |
| Example 2 | 5.7 | 8.9 | 10.5 | 0.29 | 23.6 | 99.1 |
| Example 3 | 6.1 | 11.2 | 14.9 | 0.25 | 24.5 | 100.0 |
| Example 4 | 6.3 | 9.8 | 11.5 | 0.23 | 24.0 | 100.5 |
| Example 5 | 6.2 | 9.8 | 11.7 | 0.24 | 25.0 | 101.4 |
| Example 6 | 6.2 | 9.5 | 11.2 | 0.24 | 27.0 | 101.4 |
| Example 7 | 3.5 | 5.7 | 6.8 | 0.26 | 32.0 | 100.3 |
| Comparative Example 1 | 6.4 | 9.6 | 11.1 | 0.42 | 21.0 | 94.6 |
| Comparative Example 2 | 6.6 | 11.2 | 14.7 | 0.41 | 17.5 | 96.1 |
| Comparative Example 3 | 6.8 | 10.5 | 12.4 | 0.35 | 18.5 | 96.4 |
| Comparative Example 4 | 4.1 | 7.3 | 8.9 | 0.40 | 30.0 | 96.9 |

*[1]Molar ratio of calcium atoms present as the calcium ions, relative to calcium atoms constituting the calcium hydroxide, in the calcium hydroxide-containing solution obtained in the first step
*[2]Molar ratio of sodium atoms/calcium atoms (Na/Ca) in the calcium hydroxide-containing solution obtained in the first step
*[3]Amount (mol) of sodium hydroxide added in the third step, per mole of the calcium atoms present as the calcium ions in the calcium hydroxide-containing solution obtained in the first step
*[4]In Examples 1 to 7 and Comparative Examples 2 to 4, molar ratio of total sodium atoms to total calcium atoms (Na/Ca) contained in the second dibasic calcium phosphate-containing solution) and in Comparative Example 1, molar ratio of total sodium atoms to total cacium atoms (Na/Ca) contained in the first dibasic calcium phosphate-containing solution Test Example 2

Production of Anhydrous Dibasic Calcium Phosphate Powder (Agglomerated Particles) and Evaluation of Physical Properties 1. Production of Anhydrous Dibasic Calcium Phosphate Powder (Agglomerated Particles)

Example 8

A reaction product (solid matter) was collected from the second dibasic calcium phosphate-containing solution obtained in the production process of Example 1 above, by filtration and dehydration, and washing with water. The collected reaction product (solid matter) was suspended in water to give a solids content of 30 to 40% by weight to prepare a suspension of dibasic calcium phosphate. The resulting suspension of dibasic calcium phosphate was dried with a spray dryer ("R-2" from Sakamoto Co., Ltd.) under the following drying conditions: inlet temperature 240° C., atomizer rotation speed 15000 rpm, and liquid feed rate 19 mL/minute, to obtain an anhydrous dibasic calcium phosphate powder.

Example 9

An anhydrous dibasic calcium phosphate powder was obtained under the same conditions as in Example 8, except that a reaction product (solid matter) collected from the second dibasic calcium phosphate-containing solution obtained in the production process of Example 3 above was used.

Example 10

An anhydrous dibasic calcium phosphate powder was obtained under the same conditions as in Example 8, except that a reaction product (solid matter) collected from the second dibasic calcium phosphate-containing solution obtained in the production process of Example 4 above was used.

Example 11

An anhydrous dibasic calcium phosphate powder was obtained under the same conditions as in Example 8, except that a reaction product (solid matter) collected from the second dibasic calcium phosphate-containing solution obtained in the production process of Example 7 above was used.

Comparative Example 5

An anhydrous dibasic calcium phosphate powder was obtained under the same conditions as in Example 8, except that a reaction product (solid matter) collected from the first dibasic calcium phosphate-containing solution obtained in the production process of Comparative Example 1 above was used.

Comparative Example 6

An anhydrous dibasic calcium phosphate powder was obtained under the same conditions as in Example 8, except that a reaction product (solid matter) collected from the first dibasic calcium phosphate-containing solution obtained in the production process of Comparative Example 4 above was used.

2. Methods for Evaluating Physical Properties

For the anhydrous dibasic calcium phosphate powders obtained in Examples 8 to 11 and Comparative Examples 5 and 6, the angle of repose was measured using the following method, and the particle shape was measured using the same method as that in Test Example 1 above. Moreover, for the anhydrous dibasic calcium phosphate powders obtained in Example 9, Comparative Example 5, and Comparative Example 6, the dispersibility in water was evaluated using the following method.

2-1. Angle of Repose

The anhydrous dibasic calcium phosphate powder was slowly dropped onto a dish having a diameter of 50 mm, from a position at a height of 100 mm, and at the time when a height from the bottom of the dish to the top of the anhydrous dibasic calcium phosphate powder had stabilized, the height was measured, and the angle of repose was calculated in accordance with the equation above.

2-2. Dispersibility in Water 1 g of the anhydrous dibasic calcium phosphate powder was added to 100 mL of ultrapure water, and dispersed using an ultrasonic oscillator (ASUCLEANER from AS ONE Corporation); thereafter, the dispersion was inverted and mixed, and then allowed to stand, and at 10 minutes after, the external appearance of the dispersion was checked.

3. Results of Evaluation of Physical Properties

The results of observation of the particle shapes of the anhydrous dibasic calcium phosphate powders obtained in Examples 8 to 11 confirmed that all the powders were in the form of spherical agglomerated particles in which the particles were agglomerated. On the other hand, in the anhydrous dibasic calcium phosphate powders obtained in Comparative Examples 5 and 6, the presence of agglomerated particles was partially observed, but most particles were present in a non-agglomerated state. For reference, FIGS. 4 to 7 show the results of observation of the particle shapes of the anhydrous dibasic calcium phosphate powders obtained in Example 9, Example 11, and Comparative Examples 5 and 6.

Figure 8:
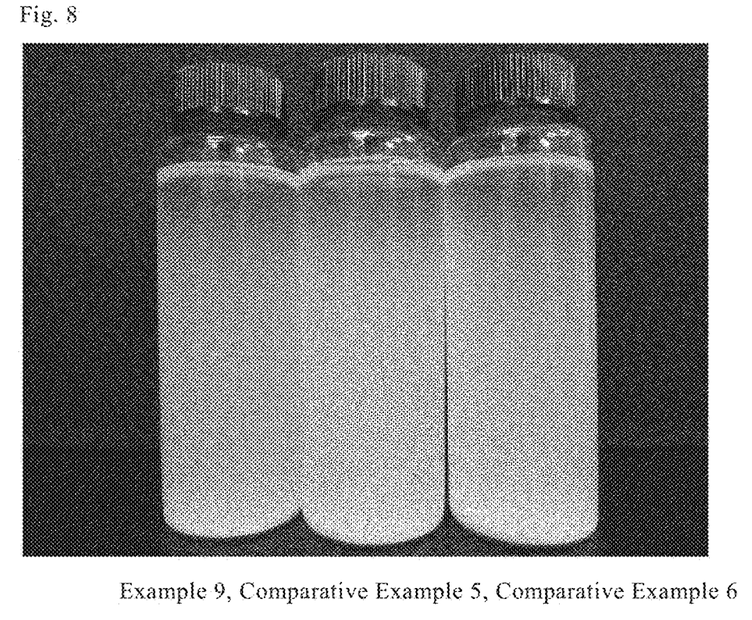
FIG. 8 is a photograph showing the results of evaluation of the dispersibility in water of the anhydrous dibasic calcium phosphate powders obtained in Example 9, and Comparative Examples 5 and 6.

Table 2 shows the results of measurement of the angle of repose, and FIG. 8 shows the results of evaluation of the dispersibility in water. The anhydrous dibasic calcium phosphate powders obtained in Examples 8 to 11 had an angle of repose of less than 45° Furthermore, the anhydrous dibasic calcium phosphate powder obtained in Example 9, despite being formed of agglomerated particles, had good dispersibility in water, which was comparable to the dispersibility in water of the anhydrous dibasic calcium phosphate powders obtained in Comparative Examples 5 and 6, in which most particles did not form agglomerated particles. That is, the results confirmed that the anhydrous dibasic calcium phosphate powders obtained by agglomerating the anhydrous dibasic calcium phosphate particles having a modal pore diameter/mean particle diameter ratio of 0.2 to 0.34 have excellent flowability, as well as excellent dispersibility in water.

TABLE 2

| | Angle of repose (°) |
|---|---|
| Example 8 | 39.2 |
| Example 9 | 38.5 |
| Example 10 | 37.9 |

TABLE 2-continued

| | Angle of repose (°) |
|---|---|
| Example 11 | 43.5 |
| Comparative Example 5 | 60.6 |
| Comparative Example 6 | 54.4 |

The invention claimed is:

1. Anhydrous dibasic calcium phosphate particles having a ratio of modal pore diameter to mean particle diameter of 0.2 to 0.34, as determined by a mercury porosimeter.

2. The method for producing anhydrous dibasic calcium phosphate according to claim 1, wherein the first step is the step of obtaining the calcium hydroxide-containing solution, by allowing a soluble calcium salt and an alkali metal hydroxide to coexist in water such that a molar ratio of alkali metal atoms relative to calcium atoms becomes 1.73 to 1.91, and the third step is the step of adding the alkali metal hydroxide to the first dibasic calcium phosphate-containing solution obtained in the second step, until a molar ratio of alkali metal atoms relative to calcium atoms in the solution becomes 1.95 to 2.5, to obtain the second dibasic calcium phosphate-containing solution.

3. The method for producing anhydrous dibasic calcium phosphate according to claim 1, wherein the alkali metal hydroxide is sodium hydroxide.

4. The method for producing anhydrous dibasic calcium phosphate according to claim 1, wherein solids are collected from the second dibasic calcium phosphate-containing solution obtained in the third step, and subjected to a drying treatment.

5. A method for producing the anhydrous dibasic calcium phosphate particles according to claim 1, the method comprising the following steps:
   (a) a first step of preparing a calcium hydroxide-containing solution, wherein the calcium hydroxide-containing solution contains calcium hydroxide and calcium ions, and a molar ratio of calcium atoms present as the calcium ions, relative to calcium atoms constituting the calcium hydroxide, is 0.04 to 0.16;
   (b) a second step of adding phosphoric acid to the calcium hydroxide-containing solution obtained in the first step to obtain a first dibasic calcium phosphate-containing solution; and
   (c) a third step of adding an alkali metal hydroxide to the first dibasic calcium phosphate-containing solution obtained in the second step, wherein the amount of the alkali metal hydroxide to be added is adjusted to 1.5 to 13.0 mol per mole of the calcium atoms present as the calcium ions in the calcium hydroxide-containing solution prepared in the first step, to obtain a second dibasic calcium phosphate-containing solution containing the anhydrous dibasic calcium phosphate particles.

6. The anhydrous dibasic calcium phosphate particles according to claim 5, wherein the anhydrous dibasic calcium phosphate particles have a mean particle diameter of 1 μm or more and less than 10 μm.

7. The anhydrous dibasic calcium phosphate particles according to claim 5, wherein the anhydrous dibasic calcium phosphate particles have a static bulk specific volume of 40 mL/10 g or less.

8. The anhydrous dibasic calcium phosphate particles according to claim 5, wherein the anhydrous dibasic calcium phosphate particles have an anhydrous dibasic calcium phosphate content of 97% or more.

9. An anhydrous dibasic calcium phosphate powder comprising agglomerated particles in which the anhydrous dibasic calcium phosphate particles according to claim 5 are agglomerated.

10. The anhydrous dibasic calcium phosphate powder according to claim 9, wherein the anhydrous dibasic calcium phosphate powder has an angle of repose of 45° or less.

* * * * *

UNITED STATES PATENT AND TRADEMARK OFFICE
CERTIFICATE OF CORRECTION

PATENT NO. : 11,261,089 B2
APPLICATION NO. : 16/499045
DATED : March 1, 2022
INVENTOR(S) : Shota Minami It is certified that error appears in the above-identified patent and that said Letters Patent is hereby corrected as shown below:

On the Title Page

Column 1 (Item (73) Assignee), Line 1, after "Ltd." insert -- Naruto (JP) --.

In the Specification

Column 6, Line 38, delete "referably" and insert -- preferably --.
Column 13, Line 17 (approx.), delete "drying" and insert -- drying; --.
Column 16, Line 28, delete "a." and insert -- a --.
Column 18, Line 16 (approx.), delete "2-5, Shape" and insert -- 2-5. Shape --.
Column 18, Line 41 (approx.), delete "7" and insert -- 1 to 7 --.
Column 18, Line 43 (approx.), delete "content." and insert -- content, --.
Column 19-20, Line 36 (Table 1-continued), delete "caclium" and insert -- calcium --.
Column 19, Line 54, delete "Sakamoto" and insert -- Sakamoto Giken --.

In the Claims

Column 22, Line 57, Claim 6, delete "claim 5," and insert -- claim 1, --.
Column 22, Line 61, Claim 7, delete "claim 5," and insert -- claim 1, --.
Column 22, Line 65, Claim 8, delete "claim 5," and insert -- claim 1, --.
Column 23, Line 3, Claim 9, delete "claim 5" and insert -- claim 1 --.

Signed and Sealed this
Fifth Day of July, 2022

Katherine Kelly Vidal
*Director of the United States Patent and Trademark Office*